United States Patent [19]

Minato

[11] Patent Number: 5,216,481
[45] Date of Patent: Jun. 1, 1993

[54] METHOD OF AND APPARATUS FOR INSPECTING TRANSPARENT OBJECT FOR DEFECT

[75] Inventor: Nobuhiro Minato, Tokyo, Japan
[73] Assignee: Toyo Glass Co., Ltd., Tokyo, Japan
[21] Appl. No.: 808,620
[22] Filed: Dec. 17, 1991

[30] Foreign Application Priority Data

Dec. 19, 1990 [JP] Japan .................................. 2-411634

[51] Int. Cl.⁵ ............................................ G01N 21/90
[52] U.S. Cl. ................................. 356/240; 250/223 B
[58] Field of Search ............... 356/237, 239, 240, 426, 356/428; 250/223 B

[56] References Cited

U.S. PATENT DOCUMENTS

| | | | |
|---|---|---|---|
| 4,376,951 | 3/1983 | Miyazawa | 356/237 X |
| 4,776,466 | 10/1988 | Yoshida | 356/428 X |
| 5,004,909 | 4/1991 | Fukuchi | 356/240 X |

FOREIGN PATENT DOCUMENTS

| | | |
|---|---|---|
| 0344617 | 6/1989 | European Pat. Off. |
| 2-49148 | 2/1990 | Japan |

Primary Examiner—Vincent P. McGraw
Attorney, Agent, or Firm—Sughrue, Mion, Zinn, Macpeak & Seas

[57] ABSTRACT

A method of and an apparatus for inspecting a transparent object for a defect wherein both of a light blocking defect and a refracting defect can be discriminated not only for presence or absence thereof but also for a shape and a kind thereof and besides discrimination of a small defect can be performed with a high degree of accuracy. According to the method, a pitch of strips of a reference striped pattern is detected in prior. Then, an object for inspection is placed at an inspecting position, and light having the reference pattern is projected upon the object and transmission light is photographed by an image sensor. A threshold value is set from an average value between two picture element data spaced from each other by one half the detected pitch, and the picture element data are successively compared with the threshold value to determine the bright or the dark thereof. A defect of the object is discriminated from numbers of picture elements determined as the bright and the dark.

12 Claims, 9 Drawing Sheets

METHOD OF AND APPARATUS FOR INSPECTING TRANSPARENT OBJECT FOR DEFECT

BACKGROUND OF THE INVENTION

1. Field of the Invention

This invention relates to a method of and an apparatus for inspecting a transparent or translucent object such as a transparent glass vessel for presence or absence of a defect and a shape, a kind and so forth of such defect.

2. Description of the Prior Art

Various methods of inspecting a body of a bottle are already known, and an exemplary one of such conventional methods is disclosed, for example, in European Patent Application Publication No. 0 344 617. According to the method, a body of a bottle is illuminated with light having a striped pattern, and a transmission image of the body is photoelectrically converted by a two-dimensional photoelectric converting apparatus. Then, the transmission image signal is scanned in a direction oblique to the direction of stripes of the striped pattern, and brightness values at least at three points adjacent the scanning line are compared with each other. Then, a noted point which is a centrally positioned one of the three points is detected as a defect point when the brightness value at the noted point is different by an amount greater than a predetermined value from brightness at the other peripheral points on the opposite sides of the noted point, and then presence or absence of a defect is determined in accordance with the thus detected defect point.

The inspecting method is based in short on the fact that, where the striped pattern is, for example, a pattern wherein white and black stripes or bands repeat alternately, if a bottle has a defect, then either a black transmission image is successively produced in a white stripe or a white transmission image is successively produced in a black stripe, by a light blocking property or a refracting property of such defect, but on the contrary if a bottle has no defect, then no such image is produced or such images are produced but discretely. Where a point A among three points A, B and C which are spaced by a predetermined distance from each other is determined as a noted point, if both of absolute values of differences in brightness between the points A and B and between the points A and C exceed a preset value, then the point A is determined as a defect point.

However, according to the conventional inspecting method, while presence or absence of a light blocking defect such as a foreign article or a soil or a refracting defect such as a foam, a line or a wrinkle, a kind or a shape of such defect cannot be discriminated. Further, where the defect is small in size, even judgment of presence or absence of such defect is difficult by picture image processing. While defects are roughly divided into those which arise from glass itself and those which arise from shaping, if a kind and a shape of a defect can be determined, than a cause of production or a process of production of such defect can be recognized, and consequently, a countermeasure for preventing such defect can be taken readily and promptly. Therefore, it is very important to discriminate a kind and a shape of a defect in order to assure stabilization in quality of products.

SUMMARY OF THE INVENTION

It is an object of the present invention to provide a method of and an apparatus for inspecting a transparent or translucent object for a defect wherein both of a light blocking defect and a refracting defect can be discriminated not only for presence or absence thereof but also for a shape and a kind thereof.

It is another object of the present invention to provide a method of and an apparatus for inspecting a transparent or translucent object for a defect wherein, even if a defect is small, discrimination of it can be performed with a high degree of accuracy.

In order to attain the objects, according to one aspect of the present invention, there is provided a method of inspecting a transparent or translucent object for a defect, which comprises the steps of projecting light having a reference pattern such as a moire wherein bright and dark portions appear successively and regularly at a predetermined pitch, receiving the pattern light directly or by way of a defect-free normal transparent article by an image sensor in the form of a solid-state image pickup element, detecting the pitch of the reference pattern of the light from numbers of picture elements of bright and dark portions of the light pattern received by the image sensor, placing an object at an inspecting position on a path of projected pattern light, projecting light having the reference pattern upon the object at the inspecting position so that light transmitted through the object may be received by the image sensor, storing data of picture elements from the image sensor into a memory, setting a threshold value from an average value between two picture element data from the memory spaced from each other by a distance corresponding to a predetermined number of picture elements with reference to the detected pitch, comparing each of the picture element data from the memory with the threshold value to determine the bright or the dark of the picture element data, discriminating a defect of the object from numbers of picture elements determined as the bright and the dark, and removing, after any step after the second light projecting step, the object from the inspecting position.

Preferably, the threshold value is determined from an average value between data of two picture element spaced from each other by a distance equal to one half the detected pitch. Preferably, at the setting step, a value obtained by adding a correction value to the average value is set as an upper threshold value while another value obtained by subtracting the correction value from the average value is set as a lower threshold value, and at the comparing step, each of the picture element data is successively compared with the upper and lower threshold values and when it falls between the upper and lower threshold values, it is determined as the dark, but in any other case, it is determined as the bright. In this instance, preferably, at the setting step, after determination of each of the picture element data between the bright and the dark with reference to the upper and lower threshold values, a number of picture elements in a unit area around the picture element is counted for each of the bright and the dark, and the bright or the dark of the picture element is determined in accordance with a difference between the numbers of the picture elements for the bright and the dark.

In accordance with the present invention, detection of a defect is principally based on the fact that, when a reference pattern such as a moire wherein the bright and the dark appear successively and regularly at a predetermined pitch is photographed through a transparent or translucent object, if the transparent or translucent object is free from a defect, the regularity of the reference pattern is maintained with the thus photographed image, but on the contrary if the transparent or translucent object has a defect, whether the defect is a light blocking defect or a refracting defect, the regularity of the reference pattern is damaged or lost. Accordingly, the pitch of the reference pattern is set to a small value comparing with a size of a defect to be detected. In this connection, with the conventional inspecting method described hereinabove, image processing is difficult unless the width and the pitch of stripes of the striped pattern are set to comparatively great values, and the accuracy in detection of a defect of a small size is deteriorated accordingly.

Thus, according to the method, a pitch of a reference pattern is detected from data obtained by photographing the reference pattern directly or through a defect-free normal transparent article. Then, the reference pattern is photographed through an object for inspection in the form of a transparent or translucent object to obtain picture element data, and the picture element data thus obtained are stored into a memory and individually judged between the bright and the dark. In this instance, an average value between data of two picture elements spaced from each other by a distance, for example, equal to one half the pitch of the reference pattern is calculated first, and a threshold value for judgment between the bright and the dark is set. If the distribution of the bright and dark of the picture element data coincides with that of the reference pattern, then the average value of the data of the two picture elements spaced by one half the pitch of the reference pattern is constant without being influenced by a variation in amount of incidence light to the image sensor. Thus, a threshold value is set from the thus calculated average value. In this instance, a predetermined correction value may be added to and subtract from the average value to obtain an upper threshold value and a lower threshold value, respectively.

Then, each of the picture element data from the memory may be compared with such upper and lower threshold values to binary digitize it such that, when it falls between the upper and lower threshold values, it is determined as "0" (that is, dark), but in any other case, it is determined as "1" (that is, bright). As a result of such binary digitization, picture elements in a portion wherein the bright and the dark appear regularly conforming to the reference pattern are almost discriminated as "1", and consequently, almost all of the dark portions are erased. In short, while elements of the picture element data which arise from the bright and the dark of the reference pattern are almost removed, the other elements where the reference pattern drops or the reference pattern appears at random due to presence of a defect will remain. After then, each of the picture elements is finally determined between the bright and the dark ("1" and "0"). In this instance, picture elements in a unit area around the picture element are taken, and a number of such picture elements is counted for each of the bright and the dark. Then, if the number of picture elements determined to be "1" (the bright) is greater than the number of the other picture elements determined to be "0" (the dark), then the average brightness in the unit area is the bright, and consequently, the picture element is finally determined as "1" (the bright) even if it is originally determined as "0" (the dark). On the contrary, if the number of picture elements determined to be "0" (the dark) is greater, then since the average brightness in the unit area is the dark, the picture element is determined as "0" (the dark) even if it is originally determined as "1" (the bright). As a result of such filtering, only those picture elements which are made the dark by a defect are extracted. Finally, the number or such picture elements is counted. Thus, from a result of such counting, presence or absence of a defect and, when a defect is present, a shape and a type of such defect, can be discriminated readily.

Thus, with the inspecting method of the present invention, when a transparent or translucent object has a defect, whether the defect is of the light blocking type or of the refracting type, not only presence of such defect but also a shape and a kind can be discriminated. Besides, even if the defect is small in size, it can be discriminated with a high degree of accuracy.

According to another aspect of the present invention, the method is accomplished with an apparatus for inspecting a transparent or translucent object for a defect, which comprises a reference pattern carrier having thereon a reference pattern such as a moire wherein the bright and the dark appear successively and regularly at a predetermined pitch, a light source for irradiating light upon the reference pattern carrier, an image sensor in the form of a solid-state image pickup element for receiving light of the reference pattern transmitted through the reference pattern carrier, memory means for receiving and storing therein data of picture elements from the image sensor, reference pattern pitch detecting means for detecting the pitch of the reference pattern from numbers of picture element data of the bright and the dark from the memory means which have been obtained from an image of the reference pattern received directly or by way of a normal transparent article by the image sensor, average value calculating means for calculating an average value between those two of the picture element data of the reference pattern from the memory means obtained from an image of the reference pattern received through an object by the image sensor which are spaced by a predetermined number of picture elements with reference to the pitch detected by the reference pattern pitch detecting means, threshold value setting means for setting upper and lower threshold values from the average value, reference pattern erasing means for successively comparing the picture element data from the memory means with the upper and lower threshold values to determine the picture element data as the dark when the picture element data fall between the upper and lower threshold values but determine the picture element data as the bright in any other case to erase data based on the reference pattern, bright/dark determining means for counting numbers of data of those picture elements in a unit area around each of the picture elements which are determined as the bright and the dark and determining the bright or the dark of the picture element in accordance with a difference between the thus counted numbers, and defect discriminating means for discriminating a defect from numbers of data of picture elements of the bright and the dark determined by the bright/dark determining means.

Thus, with the inspecting apparatus, whether a defect of a transparent or translucent object is of the light blocking type or of the refracting type, not only presence of such defect but also a shape and a kind can be discriminated. Besides, even if the defect is small in size, it can be discriminated with a high degree of accuracy.

The above and other objects, features and advantages of the present invention will become apparent from the following description and the appended claims, taken in conjunction with the accompanying drawings in which like parts or elements are denoted by like reference characters.

DESCRIPTION OF THE PREFERRED EMBODIMENT

Figure 2:
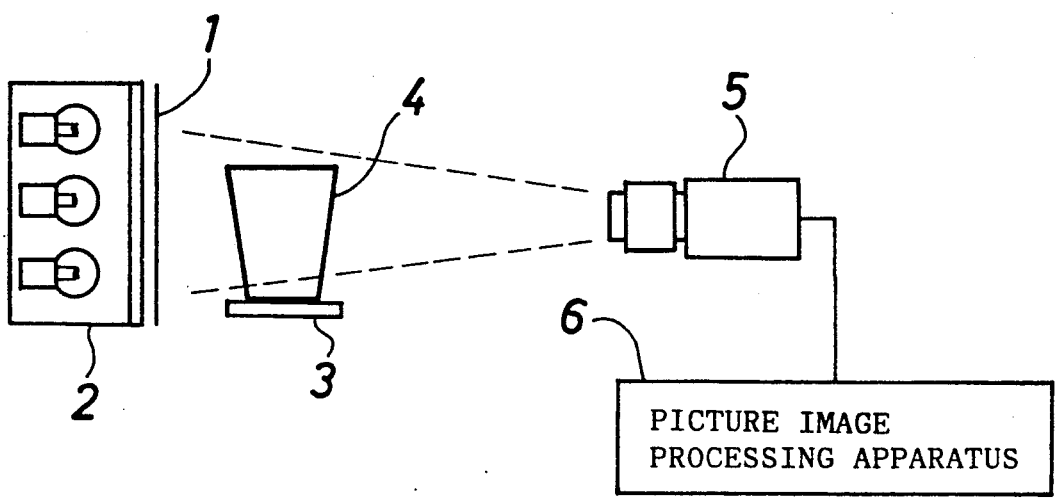
FIG. 2 is a diagrammatic representation illustrating inspection of a transparent object in accordance with an inspecting method of the present invention.

Referring first to FIG. 2, there is illustrated a manner in which a transparent or translucent object is inspected in accordance with a method of the present invention. According to the method, a reference pattern carrier 1 carrying a reference pattern thereon is illuminated by a diffusing flashlight emitting light source 2 and photographed with a two-dimensional CCD (charge coupled device) camera 5 through a body portion of a transparent or translucent object 4 such as, for example, a transparent glass transported to an inspecting position by a conveyor 3. Such photograph data are fetched into a picture image processing apparatus 6 in a timed relationship to emission of light of the diffusing flashlight emitting light source 2 and image processed by the picture image processing apparatus 6 to inspect the transparent object 4 for a defect. The picture image processing apparatus 6 includes a CPU (central processing unit), a RAM (random access memory), a ROM (read only memory) and so forth not shown.

Figure 3:
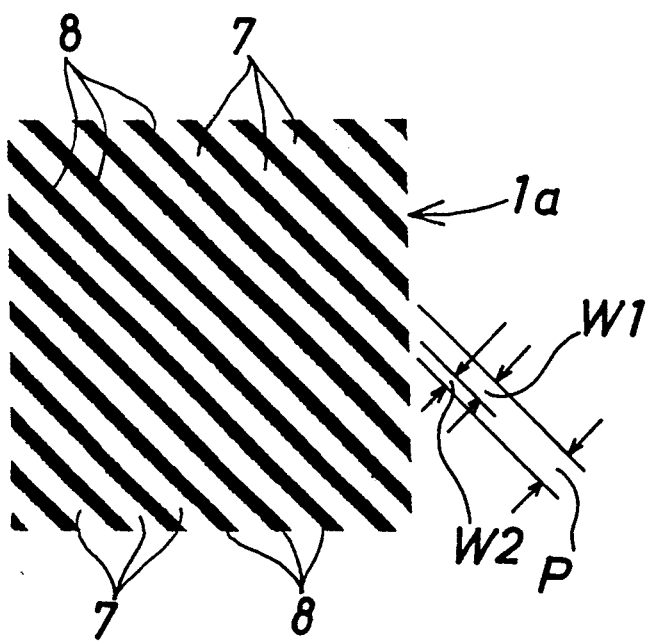
FIG. 3 is an illustrative view showing a reference pattern for use with the inspecting method.

FIG. 3 shows an example of a reference pattern which may be carried by the reference pattern carrier 1. The reference pattern 1a shown is an oblique moire wherein bright zones or stripes 7 having a width W1 and dark zones or stripes 8 having another width W2 are disposed alternately at a fixed pitch P and extend in parallel to each other. The dimensions of the widths W1 and W2 and the pitch P may be, for example, W1=0.8 mm, W2=0.5 mm, and P=1.3 mm.

Figure 4:
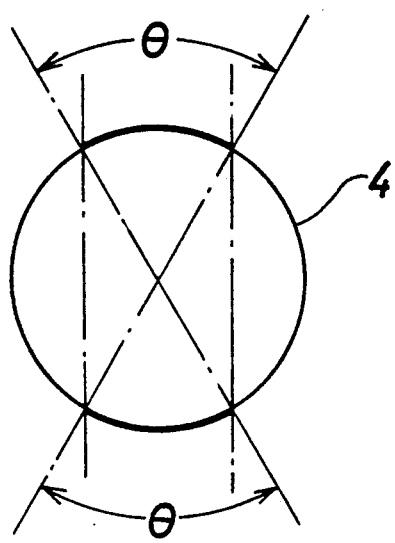
FIG. 4 is a diagrammatic view showing an inspection area of a transparent object upon inspection in accordance with the inspecting method.

Further, in order to minimize an influence of refracted light caused by a curved profile of the transparent object 4 and due to a restricted field of view of the CCD camera 5, a body portion of the transparent object 4 of an object for inspection is inspected by total of three times. In particular, referring to FIG. 4, in each inspecting operation, the body portion of the transparent object 4 is inspected only within a predetermined inspection range $\theta$ thereof, that is, the two-dimensional CCD camera 5 receives and photographs with light passing through diametrical arcuate portions of the body portion of the transparent object 4 which extend over almost 60 degrees around a center axis of the transparent object 4. After each of the first and second inspecting operations is completed, the transparent object 4 is angularly rotated by almost 60 degrees to allow different diametrical arcuate portions of the body portion of the transparent object 4 to be inspected subsequently for the predetermined inspection range $\theta$.

Figure 5:
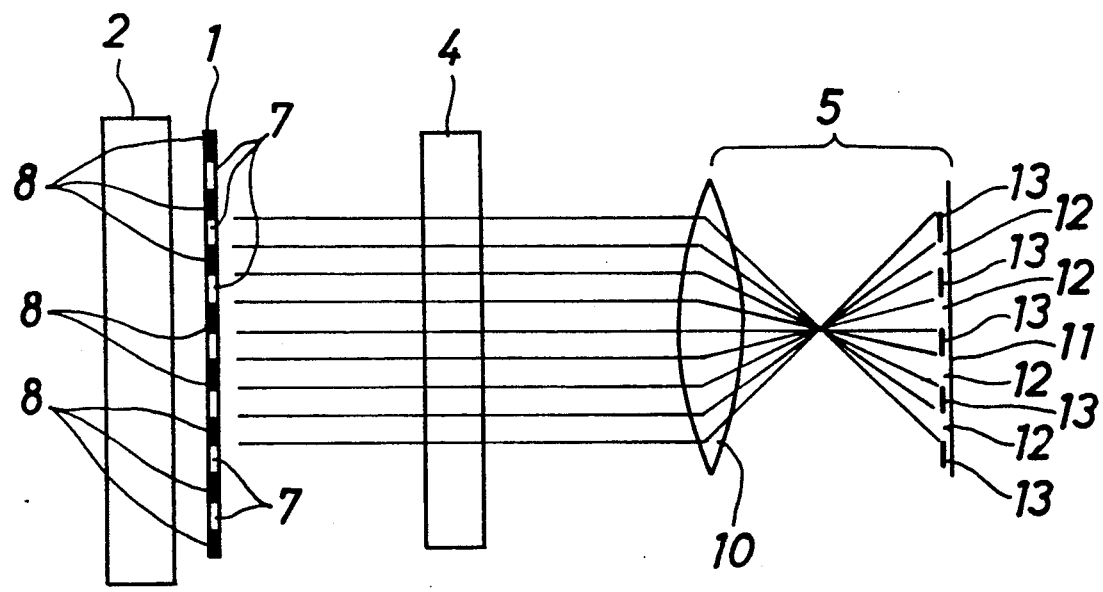
FIG. 5 is a diagrammatic representation showing a path of light when there is no defect on a transparent object upon inspection.
Figure 6:
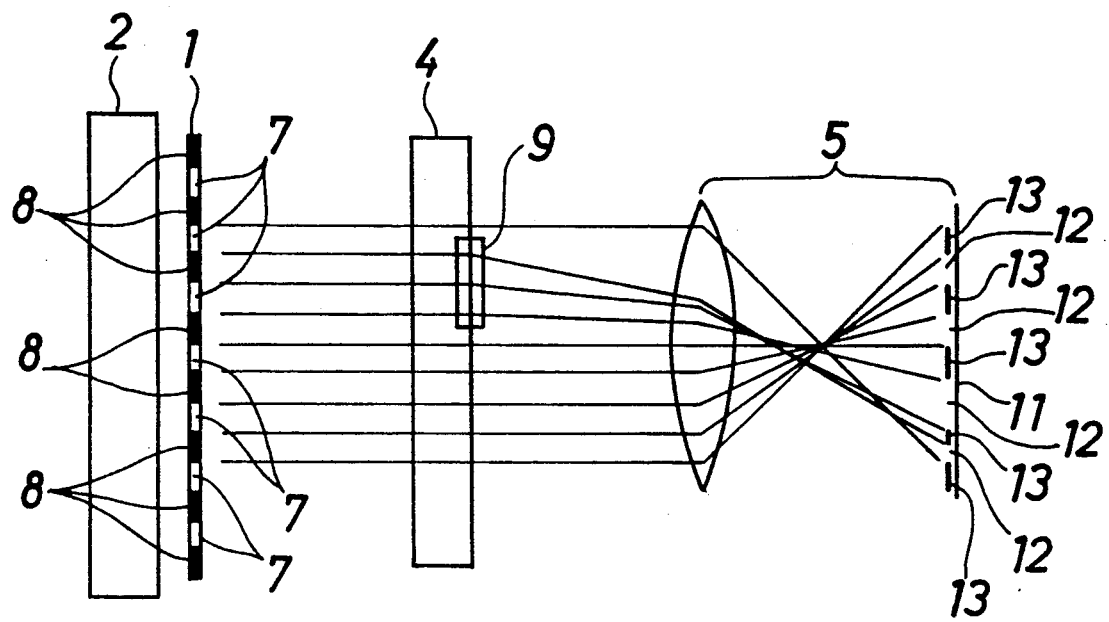
FIG. 6 is a similar view but showing a path of light when there is a defect on a transparent object.

When the transparent object 4 has no defect at the body portion thereof being inspected, light from the diffusing flashlight emitting light source 2 follows such a light path as illustrated in FIG. 5, but when it has, for example, such a refractive defective portion 9 as seen in FIG. 6, light may follow such a light path as illustrated in FIG. 6. In particular, referring to FIG. 5, when the transparent object 4 has no defect, rays of light having a pattern based on the bright stripes 7 and the dark stripes 8 of the reference pattern of the reference pattern carrier 1 pass straightforwardly through the transparent object 4 and are condensed by a lens 10 of the CCD camera 5 so that they are received as a moire image corresponding to the reference pattern of the reference pattern carrier 1; that is, having bright portions or stripes 12 and dark portions or stripes 13 which are arranged in a row with a similar width, pitch and inclination conforming to the regularity of the reference pattern of the reference pattern carrier 1 by a two-dimensional image sensor 11 (area sensor) of the CCD type. On the other hand, when the transparent object 4 has such a refractive defective portion 9 as seen in FIG. 6, rays of light are refracted by the defective portion 9, and consequently, an image received by the two-dimensional image sensor 11 has no regularity of the bright portions 12 and dark portions 13 at a portion thereof corresponding to the defective portion 9 so that the width, pitch and inclination thereof do not correspond to those of the reference pattern of the reference pattern carrier 1. This similarly applies to the case wherein the defective portion 9 is of the light blocking type.

Figure 7:
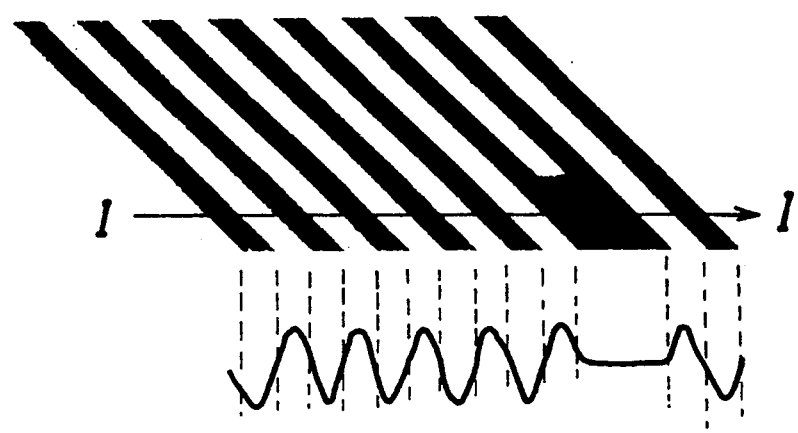
FIG. 7 is a view showing a photographed image of a reference pattern and an output waveform of an image sensor of the apparatus of FIG. 1 in contrast.
Figure 8:
FIG. 8 is a waveform diagram showing an output waveform of the image sensor when there is no defect on a transparent object and the output waveform presents a pitch conforming to a reference pitch.
Figure 9:
FIG. 9 is a similar view but showing an output waveform of the image sensor when there is a defect on a transparent object and the output waveform presents a pitch decreased by such defect.
Figure 10:
FIG. 10 is a similar view but showing an output waveform of the image sensor when there is a defect on a transparent object and the output waveform presents a pitch increased by such defect.
Figure 11:
FIG. 11 is a similar view but showing an output waveform of the image sensor when there is a defect on a transparent object and the output waveform presents a portion from which a wave or waves are dropped by such defect.

In case an image of the reference pattern of the reference pattern carrier 1 received by the image sensor 11 is such as shown in FIG. 7, if an output of the image sensor 11 is taken out from picture elements (light receiving elements), for example, along a straight line I—I, then at a portion where the regularity of the bright portions 12 and dark portions 13 is maintained, the output presents a waveform substantially similar to a sine wave, but at another particular portion where the regularity fails, for example at such a portion where, the dark portions 13 appear successively as shown in FIG. 7, a signal wave drops at such particular portion from the sine waveform. FIGS. 8 to 11 are waveform diagrams when picture element outputs of the image sensor 11 are taken out along a transverse (horizontal) row or line. In particular, FIG. 8 shows a waveform when the transparent object 4 has no defect and an image conforming to the reference pattern of the reference pattern carrier 1 is obtained. The waveform presents a sine wave which repeats at a fixed pitch P. Each of FIGS. 9, 10 and 11 shows a waveform when there is a defect, and FIG. 9 shows a waveform when the pitch is reduced due to presence of a defect; FIG. 10 shows a waveform when the pitch is increased due to presence of a defect; and FIG. 11 shows a waveform when a wave is absent.

Figure 1:
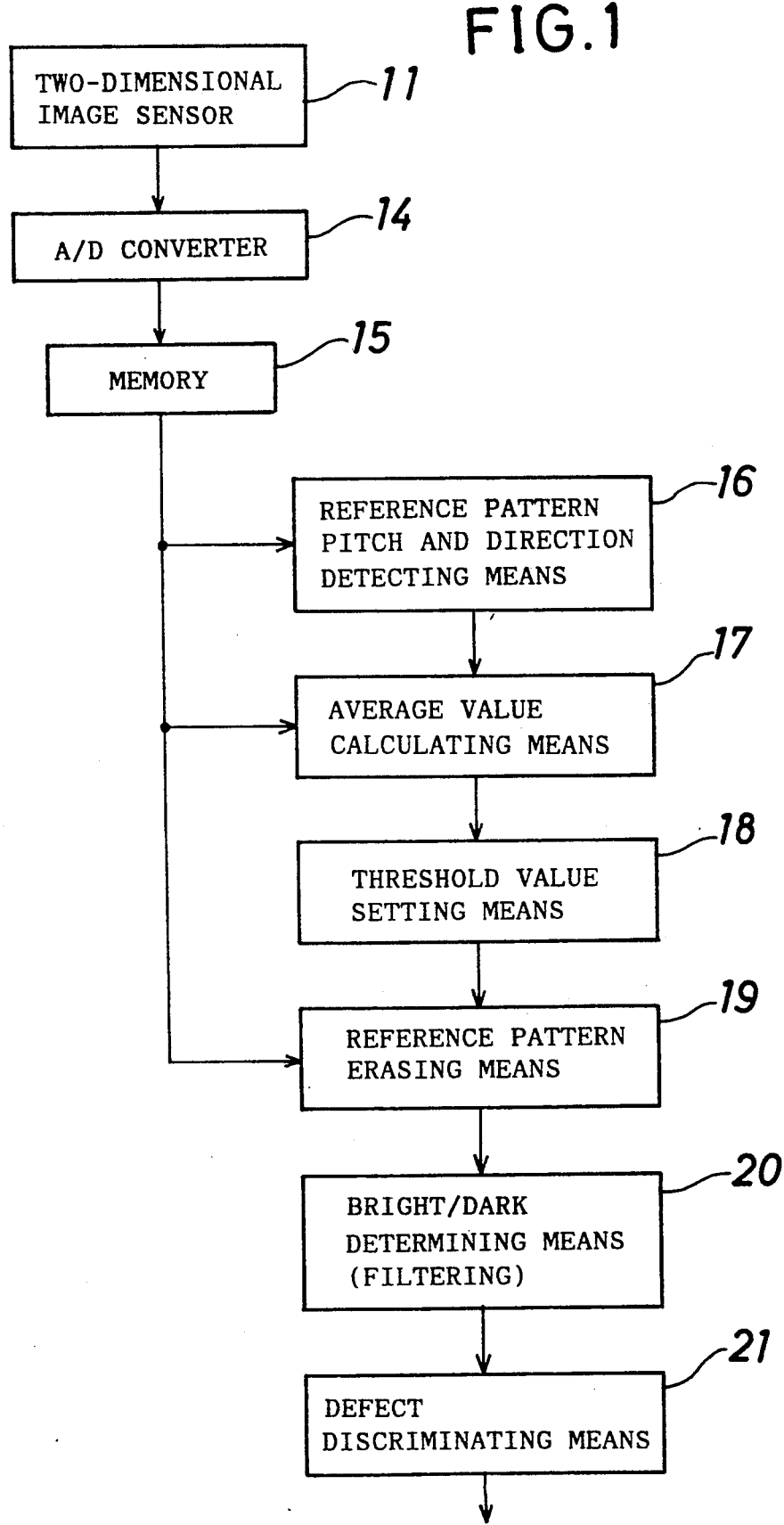
FIG. 1 is a block diagram of an apparatus for inspecting a transparent object for a defect according to the present invention.

A general construction of the picture image processing apparatus 6 is shown in FIG. 1, wherein the construction is divided in accordance with functions to be controlled by the CPU. The picture image processing apparatus 6 includes an analog-to-digital (A/D) converter 14, a memory 15, reference pattern pitch and direction detecting means 16, average value calculating means 17, threshold value setting means 18, reference pattern erasing means 19, bright/dark determining means 20 and defect discriminating means 21. An output of the two-dimensional image sensor 11 is first converted into digital data by the A/D converter 14 and then stored for each picture element into the memory 15.

Figure 12:
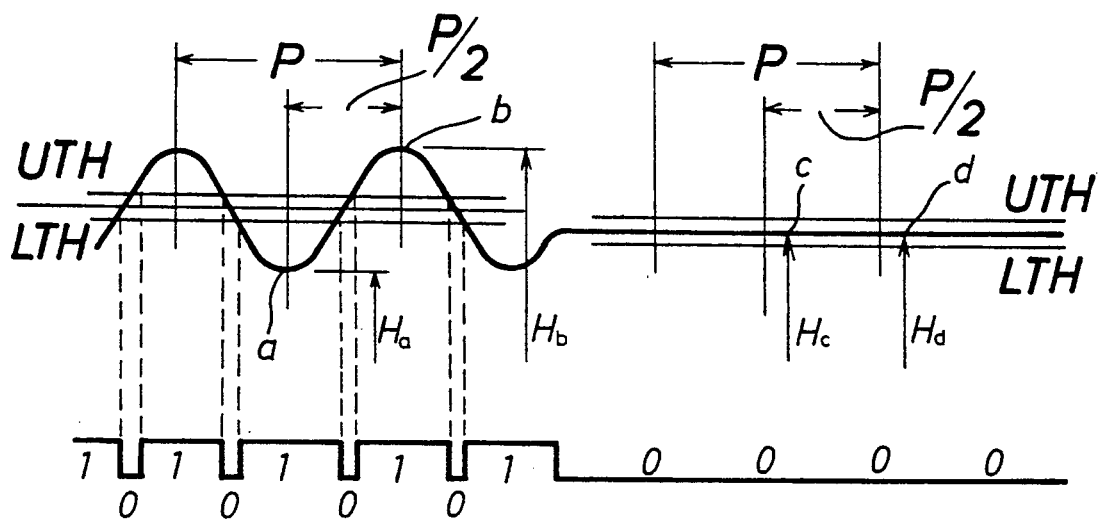
FIG. 12 is a waveform diagram illustrating a method of setting a threshold value and binary digitization in accordance with the inspecting method.

First, in order to detect a pitch P of the reference pattern of the reference pattern carrier 1, the reference pattern is photographed directly or by way of a defect-free transparent article by the CCD camera 5. In this instance, an image received by the image sensor 11 of the CCD camera 5 conforms to the regularity of the reference pattern of the reference pattern carrier 1 as described above and a waveform of a signal thus taken out presents a sine wave. The reference pattern pitch and direction detecting means 16 detects the pitch P of the reference pattern from a number of picture elements corresponding to a repeat period of the sine wave and also detects a direction of inclination of the reference pattern 1. A technique of picture image processing with reference to such sine wave is illustrated in FIG. 12. It is to be noted that, while the picture image processing is actually performed by digital processing of digital data for each picture element taken out from the image sensor 11 and stored into and read out from memory 15, description thereof will be provided in an analog fashion with the waveform of FIG. 12 for the convenience of description.

After the pitch P and the inclination direction of the reference pattern are detected by the reference pattern pitch and direction detecting means 16, transparent or translucent objects 4 as objects for inspection are transported successively and stepwise by the conveyor 3 to the inspection position. At the inspecting position, the reference pattern 1 is photographed through a transparent object 4 by the image sensor 11. Data obtained from the image sensor 11 by such photographing are stored for each picture element into the memory 15. The average value calculating means 17 refers to the detected pitch P (360 degrees in phase of the sine wave) and inclination direction of the reference pattern, takes out picture element data of two points displaced by the one half pitch, in short, by P/2, in phase (180 degrees) from each other, repeats this for a plurality of locations for the bright and dark portions or stripes, and calculates an average value among picture element data from the bright portions (average value among maximum brightness values from the bright portions) and an average value among the dark portions (average value among minimum brightness values from the plurality of dark portions). Now, where brightness values at points a and b spaced by P/2 from each other in a portion in which the reference pattern 1 exists in FIG. 12 are represented by Ha and Hb, respectively, then an average value is given by (Ha+Hb)/2. Meanwhile, where brightness values at points c and d spaced by P/2 in another portion in which the reference pattern does not exist or the reference pattern is out of order are represented by Hc and Hd, respectively, an average value is given by (Hc+Hd)/2. It is to be noted that, while the pitch for the calculation of an average value is preferably set to one half the pitch P of the reference pattern, it need not set to such specific value.

The threshold value setting means 18 adds a predetermined correction value $\alpha$ to the average value (Ha+Hb)/2 or (Hc+Hd)/2 calculated by the average value calculating means 17 to set an upper threshold value UTH=(Ha+Hb)/2+$\alpha$ or UTH=(Hc+Hd)/2+$\alpha$ and subtracts the correction value $\alpha$ from the average value (Ha+Hb)/2 or (Hc+Hd)/2 to set a lower threshold value LTH=(Ha+Hb)/2−$\alpha$ or LTH=(Hc+Hd)/2−$\alpha$.

The reference pattern erasing means 19 compares each of the picture element data stored in the memory 15 with the upper threshold value UTH and lower threshold value LTH to binary digitize the picture element data such that, when the picture element data fall between the upper and lower threshold values UTH and LTH, they are represented as "0" (that is, dark), but in any other case, the picture element data are represented as "1" (that is, bright) as shown in FIG. 12 (such binary digitized signals are shown at a lower portion of FIG. 12).

Picture elements in a portion wherein bright and dark portions or stripes appear regularly in a horizontal direction conforming to the reference pattern of the reference pattern carrier 1 as a result of such binary digitizing processing are almost discriminated as "1", and consequently, almost all of the dark portions of the reference pattern 1 are erased. In short, while the dark portions provided by the reference pattern are almost removed, a dark portion (0 in binary number) where the reference pattern drops or another dark portion where the reference pattern appears at random due to presence of a defect will remain.

While dark portions (0 in binary number) having such regularity as originating from the reference pattern of the reference pattern carrier 1 will remain a little as shown in FIG. 12 even by such binary digitization by the reference pattern erasing means 19 as described above, the size of the remaining dark portions (consecutive number of picture elements for which a brightness value is discriminated as 0) is smaller than the size of dark portions originating from a defect. Thus, the bright/dark determining means 20 finally determines, after temporary binary digitization by the reference pattern erasing means 19, the bright or the dark for each picture element by such filtering processing as described below from a relationship to a plurality of picture elements therearound. Different techniques of such filtering are illustrated in FIGS. 13 and 14.

Figure 13:
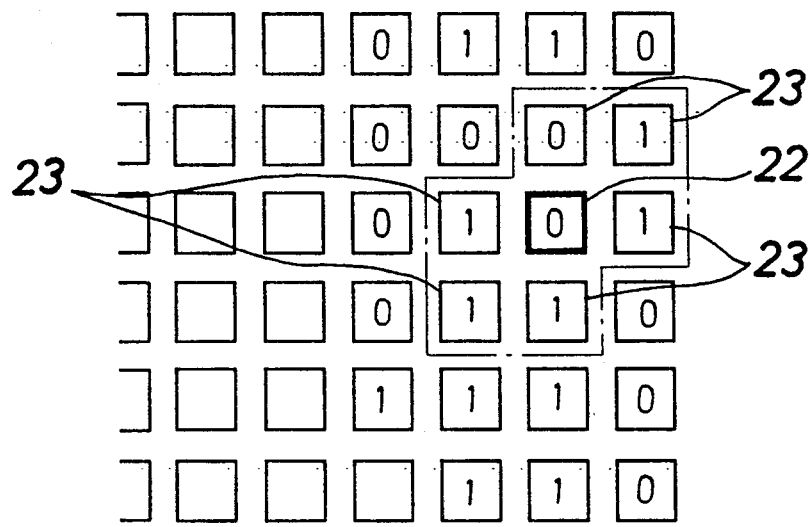
FIG. 13 is a diagrammatic representation illustrating a technique of filtering processing in accordance with the inspecting method.
Figure 14:
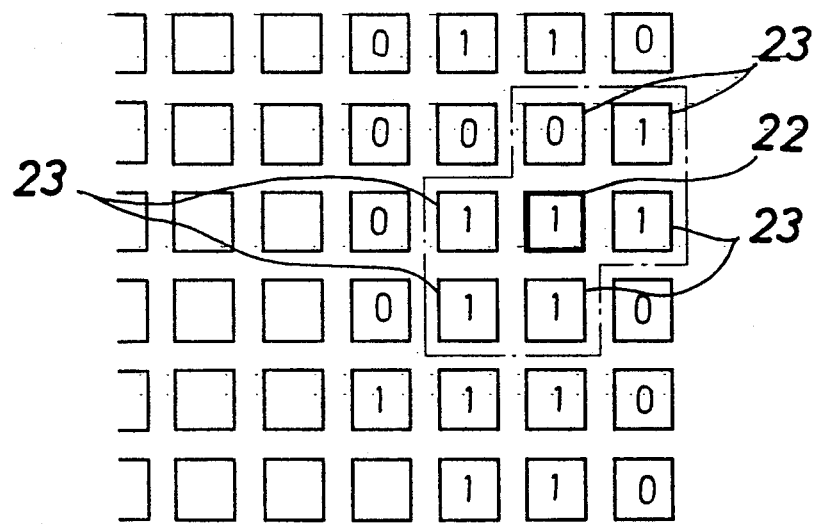
FIG. 14 is a view illustrating an alternative technique of filtering processing.

Referring now to FIG. 13, it is assumed that a certain picture element 22 is discriminated temporarily as "0" as a result of binary digitization by the reference pattern erasing means 19. In finally determining whether the picture element 22 is "1" or "0", a number of those picture elements in a group of picture elements per unit area including the picture element 22 and picture elements 23 around the picture element 22 which are discriminated as "1" and another number of those picture elements of the group of picture elements which are discriminated as "0" are counted individually. Then, one of the binary values having a greater count number is determined as a binary value of the picture element 22. In the case of the picture elements shown in FIG. 13, the number of picture elements of "1" exceeds one half, and accordingly, the picture element 22 is changed from "0" to "1" as seen from FIG. 14. In other words, an average brightness value is calculated for a group of picture elements for a unit area, and if it is higher than a predetermined brightness value, then the picture element at the center of the unit area is determined as "1" (bright). As a result of such processing, the dark portions of the reference pattern 1 remaining after processing by the reference pattern erasing means 19 are removed, and only dark portions arising from a defect are extracted.

The defect discriminating means 21 counts a number of picture elements at that portion of picture elements after determination between the bright and the dark by the bright/dark determining means 20 in which "0" appears successively in a horizontal direction and a vertical direction or further in an oblique direction, and when the count value is higher than a predetermined value, the defect discriminating means 21 discriminates that a defect is present and outputs an excluding signal for excluding the transparent object 4 as an object for inspection. Further, a shape or a kind of the defect is discriminated from the number of the thus counted picture elements in accordance with a known pattern recognizing technique.

Figure 15:
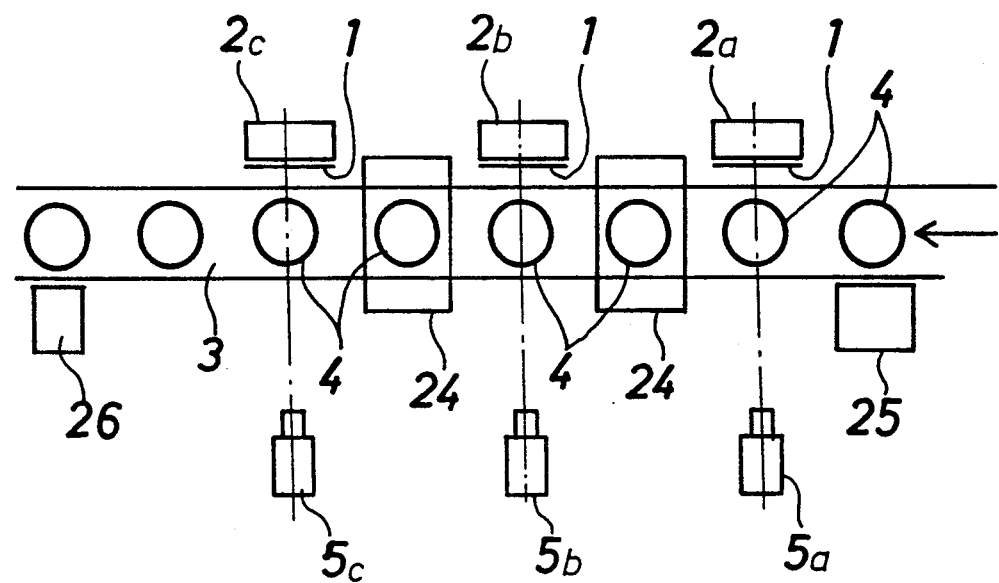
FIG. 15 is a schematic plan view illustrating an inspecting operation with an inspecting equipment in which the inspecting apparatus shown in FIG. 1 is incorporated.
Figure 17:
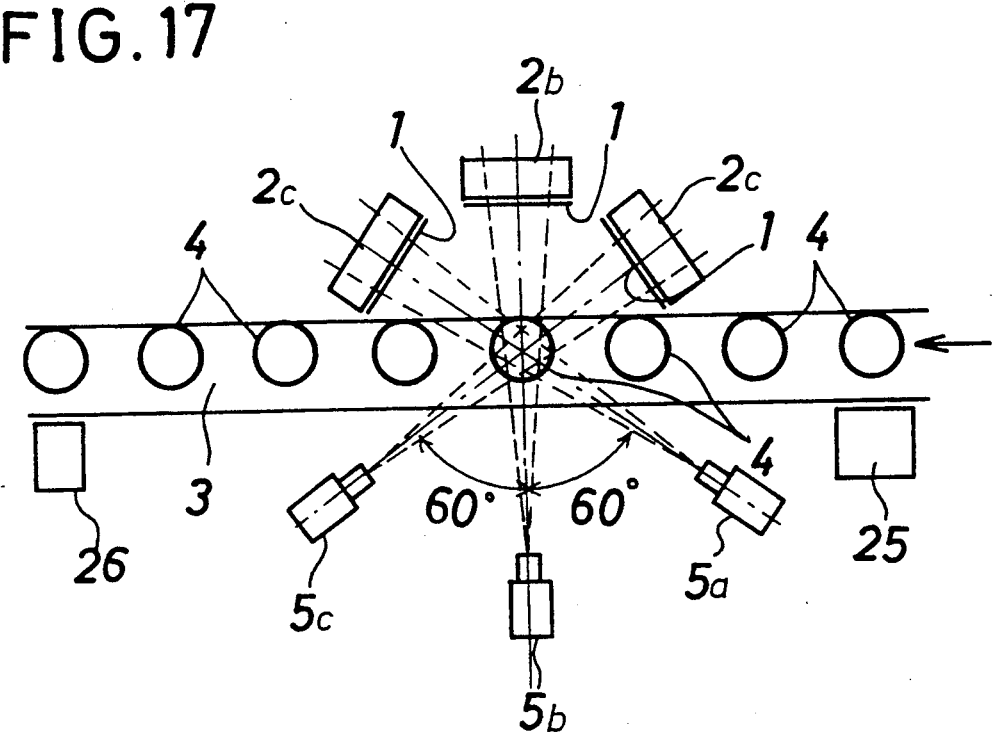
FIG. 17 is a similar view illustrating a further inspecting operation with another modified inspecting equipment.

FIGS. 15 and 17 show different manners of inspection and different inspecting equipments to which an inspecting method of the present invention is applied. Referring first to FIG. 15, the inspecting equipment shown includes three sets of light sources and CCD cameras including a first light source 2a and a first CCD camera 5a, a second light source 2b and a second CCD camera 5b, and a third light source 2c and a third CCD camera 5c. The three sets are disposed in a spaced relationship from each other in a transporting direction of a conveyor 3, that is, in the direction indicated by an arrow mark, and two (first and second) rotating apparatus 24 are installed between the first and seconds sets and between the second and third sets, respectively. One third of a body portion of a transparent or translucent object 4 is photographed by the first CCD camera 5a, and then the transparent object 4 is transported to the first rotating apparatus 24, at which it is rotated by 60 degrees. Then, it is transported again to an inspecting position by the second set, at which a next one third of the transparent object 4 is photographed by the second CCD camera 5b. The transparent object 4 is then transported to the second rotating device 24 and rotated further by 60 degrees, whereafter it is transported to an inspecting position by the third set and a remaining one third of the transparent object 4 is photographed by the third CCD camera 5c. It is to be noted that reference numeral 25 denotes a velocity detecting apparatus for detecting a velocity of the conveyor 3, and 26 denotes an excluding apparatus for excluding from the conveyor 3 a transparent object 4 which has been discriminated as having a defect by the defect discriminating means 21.

Figure 16:
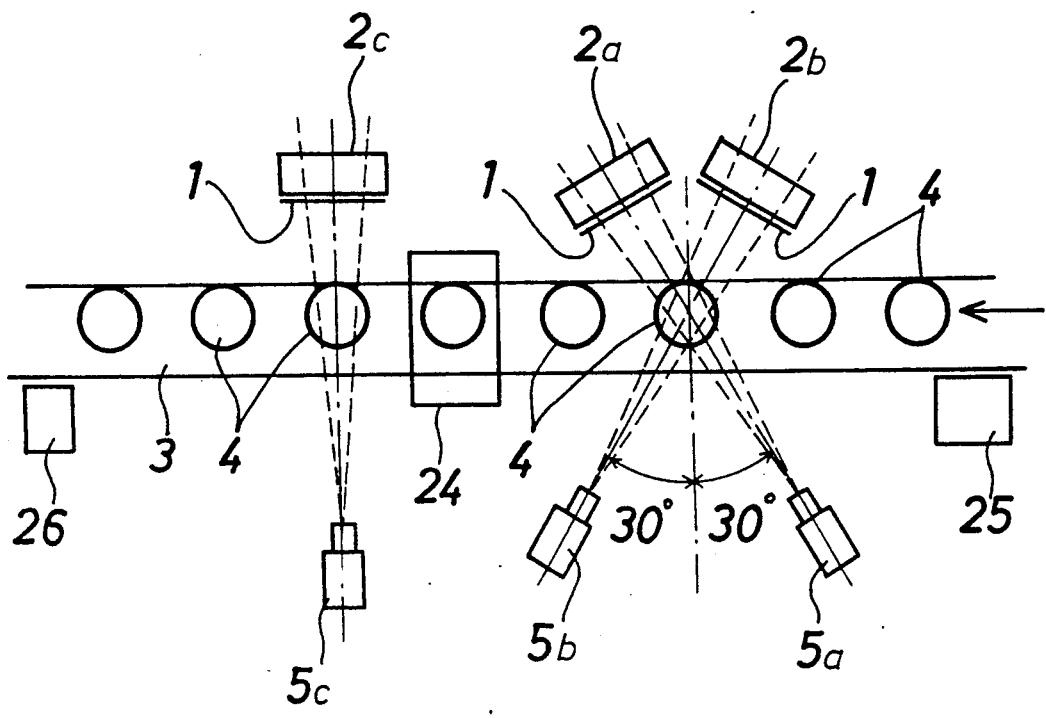
FIG. 16 is a similar view illustrating another inspecting operation with a modified inspecting equipment.

In the case of the inspecting equipment of FIG. 16, a first set of a light source 2a and a CCD camera 5a and a second set of a light source 2b and a CCD camera 5b are disposed such that optical axes of them may make an angle of 60 degrees and cross each other at an inspecting position on a conveyor 3 while a third set of a light source 2c and a CCD camera 5c is disposed in a spaced relationship from the first and second sets such that a different one third of a body portion of a transparent or translucent object 4 is first photographed at the inspecting position by each of the CCD cameras 5a and 5b of the first and second sets, and then the transparent object 4 is transported to and rotated by 90 degrees by a rotating apparatus 24, whereafter the remaining one third of the transparent object 4 is photographed by the CCD camera 5c of the third set.

In case of the inspecting equipment shown in FIG. 17, three sets of light sources and CCD cameras are disposed such that they may make an angle of 60 degrees between them so that a different one third of a body portion of a transparent of translucent object 4 may be photographed at a same inspecting position by each of them.

Figure 18:
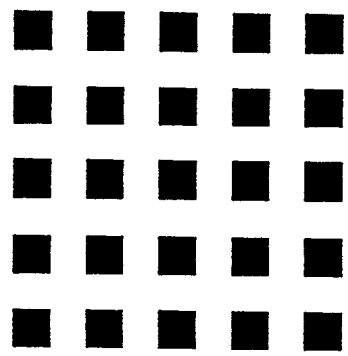
FIG. 18 is an illustrative view showing an alternative reference pattern for use with the inspecting method.
Figure 19:
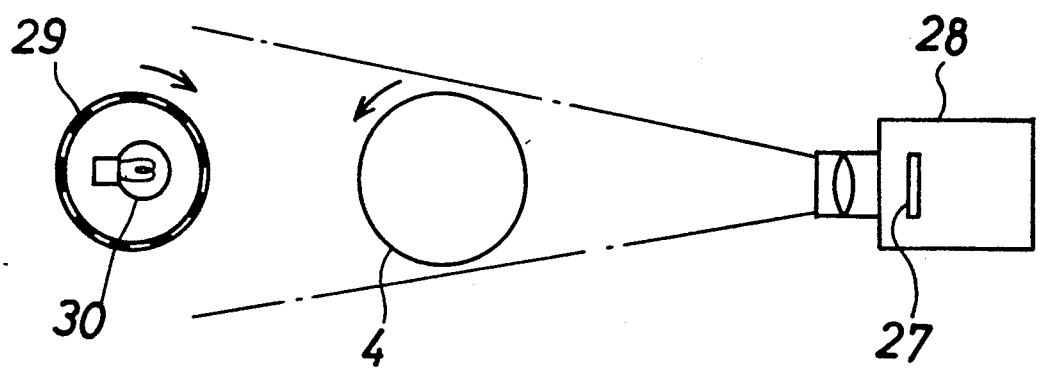
FIG. 19 is a diagrammatic view illustrating alternative inspection in accordance with the present invention wherein an inspection is performed using a one-dimensional CCD camera.

Having now fully described the invention, it will be apparent to one of ordinary skill in the art that many changes and modifications can be made thereto without departing from the spirit and scope of the invention as set forth herein. For example, while the reference pattern 1a of the reference pattern carrier 1 is an oblique moire in the inspecting apparatus described hereinabove with reference to FIG. 2, it may otherwise be such a pattern similar to a checker board pattern as shown in FIG. 18 or may be any pattern wherein the bright and the dark appear successively and regularly at a predetermined pitch. Further, while two threshold values including an upper threshold value and a lower threshold value are employed, discrimination between the bright and the dark may be performed with reference to a single threshold value. Furthermore, while the two-dimensional CCD camera 5 is used and an inspecting operation is performed in a condition wherein each of reference pattern carrier 1 having the reference pattern and a transparent or translucent object 4 is left fixed, an inspecting operation may be performed while a transparent or translucent object 4 is being rotated. Further, an inspecting operation for a defect can be performed by the similar processing to that described above but in a different manner wherein, using a one-dimensional CCD camera 28 including a one-dimensional image sensor (line sensor) 27 as shown in FIG. 19, a tubular reference pattern carrier 30 having a reference pattern thereon is rotated around a light source 30 while at the same time a transparent or translucent object 4 is rotated.

What is claimed is:

1. A method of inspecting a transparent or translucent object for a defect, comprising the steps of:
   projecting light having a reference pattern such as a moire wherein bright and dark portions appear successively and regularly at a predetermined pitch;
   receiving the pattern light directly or by way of a defect-free normal transparent article by an image sensor in the form of a solid-state image pickup element;
   detecting the pitch of the reference pattern of the light from numbers of picture elements of bright and dark portions of the light pattern received by said image sensor;
   placing an object at an inspecting position on a path of projected pattern light;
   projecting light having the reference pattern upon the object at the inspecting position so that light transmitted through the object may be received by said image sensor;
   storing data of picture elements from said image sensor into a memory;
   setting a threshold value from an average value between two picture element data from said memory spaced from each other by a distance corresponding to a predetermined number of picture elements with reference to the detected pitch;
   comparing each of the picture element data from said memory with the threshold value to determine the bright or the dark of the picture element data;
   discriminating a defect of the object from numbers of picture elements determined as the bright and the dark; and
   removing, after any step after the second light projecting step, the object from the inspecting position.

2. A method as claimed in claim 1, wherein the threshold value is determined from an average value between data of two picture elements spaced from each other by a distance equal to one half the detected pitch.

3. A method as claimed in claim 1, wherein, at the setting step, a value obtained by adding a correction value to the average value is set as an upper threshold value while another value obtained by subtracting the correction value from the average value is set as a lower threshold value, and at the comparing step, each of the picture element data is successively compared with the upper and lower threshold values and when it falls between the upper and lower threshold values, it is determined as the dark, but in any other case, it is determined as the bright.

4. A method as claimed in claim 3, wherein, at the setting step, after determination of each of the picture element data between the bright and the dark with reference to the upper and lower threshold values, a number of picture elements in a unit area around the picture element is counted for each of the bright and the dark, and the bright or the dark of the picture element is determined in accordance with a difference between the numbers of the picture elements for the bright and the dark.

5. A method as claimed in claim 1, wherein, after the removing step, a new object is placed at the inspecting position and the steps from the second projecting step to the removing step are repeated to perform inspection of the new object for a defect.

6. A method as claimed in claim 1, wherein, at the second light projecting step, light having the reference pattern is projected diametrically upon the object at the inspecting position over an angle of about 60 degrees around an axis of the object so that light transmitted through the object may be received by said image sensor, and further comprising the step of rotating, after the second light projecting step or after any step after then, the object around the axis thereof by 60 degrees twice, the steps from the storing step to the discriminating step being repeated after each rotation of the object by 60 degrees to perform inspection of the entire object for a defect.

7. An apparatus for inspecting a transparent or translucent object for a defect, comprising:
   a reference pattern carrier having thereon a reference pattern such as a moire wherein the bright and the dark appear successively and regularly at a predetermined pitch;
   a light source for irradiating light upon said reference pattern carrier;
   an image sensor in the form of a solid-state image pickup element for receiving light of the reference pattern transmitted through said reference pattern carrier;
   memory means for receiving and storing therein data of picture elements from said image sensor;
   reference pattern pitch detecting means for detecting the pitch of the reference pattern from numbers of picture element data of the bright and the dark from said memory means which have been obtained from an image of the reference pattern received directly or by way of a normal transparent article by said image sensor;
   average value calculating means for calculating an average value between those two of the picture element data of the reference pattern from said memory means obtained from an image of the reference pattern received through an object by said image sensor which are spaced by a predetermined number of picture elements with reference to the pitch detected by said reference pattern pitch detecting means;
   threshold value setting means for setting upper and lower threshold values from the average value;
   reference pattern erasing means for successively comparing the picture element data from said memory means with the upper and lower threshold values to determine the picture element data as the dark when the picture element data fall between the upper and lower threshold values but determine the picture element data as the bright in any other case to erase data based on the reference pattern;
   bright/dark determining means for counting numbers of data of those picture elements in a unit area around each of the picture elements which are determined as the bright and the dark and determining the bright or the dark of the picture element in accordance with a difference between the thus counted numbers; and defect discriminating means for discriminating a defect from numbers of data of picture elements of the bright and the dark determined by said bright-/dark determining means.

8. An apparatus as claimed in claim 7, wherein said average value calculating means calculates an average value between those two of the picture element data of the reference pattern from said memory means obtained from an image of the reference pattern received through an object by said image sensor which are spaced by a distance equal to one half the detected pitch.

9. An apparatus as claimed in claim 7, wherein said threshold value setting means sets upper and lower threshold values by adding and subtracting a correction value to and from the average value, respectively.

10. An equipment for inspecting a transparent or translucent object for a defect, comprising:

means for successively positioning an object at first, second and third inspecting positions;

an optical system provided for each of the first, second and third inspective positions for projecting light of a reference pattern diametrically upon an object at the inspecting position over an angle of about 60 degrees around an axis of the object and photographing light transmitted through the object to obtain data of picture elements of an image of the received light;

a rotating apparatus interposed between the first and second inspecting positions and between the second and third inspecting positions for rotating an object by 60 degrees in one direction around its axis; and a picture image processing apparatus connected to each or all of the optical systems for detecting a defect of an object from the data of picture elements from said optical system or systems, wherein said picture image processing apparatus or each of said picture image processing apparatus includes:

memory means for receiving and storing therein data of picture elements from the corresponding optical system or the optical systems;

reference pattern pitch detecting means for detecting the pitch of the reference pattern from numbers of picture element data of the bright and the dark from said memory means which have been obtained from an image of the reference pattern received directly or by way of a normal transparent article by said optical system;

average value calculating means for calculating an average value between those two of the picture element data of the reference pattern from said memory means obtained from an image of the reference pattern received through an object by said optical system which are spaced by a predetermined number of picture elements with reference to the pitch detected by said reference pattern pitch detecting means;

threshold value setting means for setting upper and lower threshold values from the average value;

reference pattern erasing means for successively comparing the picture element data from said memory means with the upper and lower threshold values to determine the picture element data as the dark when the picture element data fall between the upper and lower threshold values but determine the picture element data as the bright in any other case to erase data based on the reference pattern;

bright/dark determining means for counting numbers of data of those picture elements in a unit area around each of the picture elements which are determined as the bright and the dark and determining the bright or the dark of the picture element in accordance with a difference between the thus counted numbers; and defect discriminating means for discriminating a defect from numbers of data of picture elements of the bright and the dark determined by said bright-/dark determining means.

11. An equipment for inspecting a transparent or translucent object for a defect, comprising:

means for successively positioning an object at a pair of inspecting positions;

first and second optical systems provided for one of the inspecting positions for projecting light of a reference pattern diametrically upon an object at the inspecting position over different contiguous angular ranges of about 60 degrees around an axis of the object and photographing light transmitted through the object to obtain data of picture elements of images of the received light;

a third optical system provided for the other of the inspecting positions for projecting light of the same reference pattern diametrically upon an object at the inspecting position over an angular range of about 60 degrees around the axis of the object and photographing light transmitted through the object to obtain data of picture elements of an image of the received light;

a rotating apparatus interposed between the inspecting positions for rotating an object by 60 degrees in one direction around its axis so that said first, second and third optical systems may photograph different contiguous angular ranges of an object; and a picture image processing apparatus connected to each or all of said first to third optical systems for detecting a defect of an object from the data of picture elements from said optical system or systems, wherein said picture image processing apparatus or each of said picture image processing apparatus includes:

memory means for receiving and storing therein data of picture elements from the corresponding optical system or the optical systems;

reference pattern pitch detecting means for detecting the pitch of the reference pattern from numbers of picture element data of the bright and the dark from said memory means which have been obtained from an image of the reference pattern received directly or by way of a normal transparent article by said optical system;

average value calculating means for calculating an average value between those two of the picture element data of the reference pattern from said memory means obtained from an image of the reference pattern received through an object by said optical system which are spaced by a predetermined number of picture elements with reference to the pitch detected by said reference pattern pitch detecting means;

threshold value setting means for setting upper and lower threshold values from the average value;

reference pattern erasing means for successively comparing the picture element data from said memory means with the upper and lower threshold values to determine the picture element data as the dark when the picture element data fall between the upper and lower threshold values but determine the picture element data as the bright in any other case to erase data based on the reference pattern;

bright/dark determined means for counting numbers of data of those picture elements in a unit area around each of the picture elements which are determined as the bright and the dark and determining the bright or the dark of the picture element in accordance with a difference between the thus counted numbers; and defect discriminating means for discriminating a defect from numbers of data of picture elements of the bright and the dark determined by said bright-/dark determining means.

12. An equipment for inspecting a transparent or translucent object for a defect, comprising:

means for successively positioning an object at an inspecting position;

first, second and third optical systems provided for the inspecting position for projecting light of a reference pattern diametrically upon an object at the inspecting position over different contiguous angular ranges of about 60 degrees around an axis of the object and photographing light transmitting through the object to obtain data of picture elements of images of the received light; and a picture image processing apparatus connected to each or all of said first to third optical systems for detecting a defect of an object from the data of picture elements from said optical system or systems, wherein said picture image processing apparatus or each of said picture image processing apparatus includes:

memory means for receiving and storing therein data of picture elements from the corresponding optical system or the optical systems;

reference pattern pitch detecting means for detecting the pitch of the reference pattern from numbers of picture element data of the bright and the dark from said memory means which have been obtained from an image of the reference pattern received directly or by way of a normal transparent article by said optical system;

average value calculating means for calculating an average value between those two of the picture element data of the reference pattern from said memory means obtained from an image of the reference pattern received through an object by said optical system which are spaced by a predetermined number of picture elements with reference to the pitch detected by said reference pattern pitch detecting means;

threshold value setting means for setting upper and lower threshold values from the average value;

reference pattern erasing means for successively comparing the picture element data from said memory means with the upper and lower threshold values to determined the picture element data as the dark when the picture element data fall between the upper and lower threshold values but determined the picture element data as the bright in any other case to erase data based on the reference pattern;

bright/dark determining means for counting numbers of data of those picture elements in a unit area around each of the picture elements which are determined as the bright and the dark and determining the bright or the dark of the picture element in accordance with a difference between the thus counted numbers; and defect discriminating means for discriminating a defect from numbers of data of picture elements of the bright and the dark determined by said bright-/dark determining means.

* * * * *